United States Patent [19]

Gaertner

[11] 4,251,256
[45] Feb. 17, 1981

[54] HERBICIDAL N-SUBSTITUTED ETHYLENE DERIVATIVES OF N-PHOSPHONOMETHYLGLYCINE

[75] Inventor: Van R. Gaertner, Ballwin, Mo.

[73] Assignee: Monsanto Company, St. Louis, Mo.

[21] Appl. No.: 972,546

[22] Filed: Dec. 22, 1978

[51] Int. Cl.³ .......................... A01N 57/12; C07F 9/40
[52] U.S. Cl. ........................................ 71/86; 260/940; 560/155
[58] Field of Search ............................ 71/86; 260/940; 560/155

[56] References Cited

U.S. PATENT DOCUMENTS

| | | | |
|---|---|---|---|
| 3,799,758 | 3/1974 | Franz | 71/86 |
| 3,835,000 | 9/1974 | Frazier et al. | 71/86 |
| 3,991,095 | 11/1976 | Gaertner | 71/87 X |
| 4,062,669 | 12/1977 | Franz | 71/86 |
| 4,067,719 | 10/1978 | Dutra | 71/86 |
| 4,119,430 | 10/1978 | Gaertner et al. | 71/86 |
| 4,130,412 | 12/1978 | Franz | 71/86 |

Primary Examiner—Catherine L. Mills
Attorney, Agent, or Firm—Arnold H. Cole; Donald W. Peterson

[57] ABSTRACT

Certain N-substituted ethylene derivatives of N-phosphonomethylglycine are novel compounds and display useful post-emergent herbicidal activity.

9 Claims, No Drawings

HERBICIDAL N-SUBSTITUTED ETHYLENE DERIVATIVES OF N-PHOSPHONOMETHYLGLYCINE

This invention relates to novel organic chemical compounds. More particularly, this invention is concerned with a pair of derivatives of N-phosphonomethylglycine in which the nitrogen atom contains a substituted ethylene group thereon. These compounds have been found to display useful and unexpected activity in the post-emergent control of undesired plants.

U.S. Pat. No. 3,799,758 describes N-phosphonomethylglycine and salts, esters and amides thereof for use as herbicides. All of such compounds must contain a hydrogen atom on the central nitrogen atom. U.S. Pat. No. 4,062,669 describes a class of N-oxides of N-phosphonomethylglycine where the central nitrogen atom must contain a substituent group thereon, and that group can be an aliphatic hydrocarbon, a substituted aliphatic hydrocarbon, a hydrocarbonoxyalkyl or a methylene phosphonic group. These compounds are described as useful herbicides, and they are prepared by oxidation of corresponding compounds which do not have the N-oxide group.

It has now been found, in accordance with the present invention, that two of the compounds within the generic disclosure of starting materials in the latter patent, possess useful and unexpected activity as post-emergent herbicides. Other closely related starting materials also within said generic disclosure are either wholly inactive or display a much lower level of such herbicidal activity.

The two compounds of this invention are the monosodium salt of ethyl N-(2-cyanoethyl)-N-phenoxyphosphonomethylglycinate which has the formula

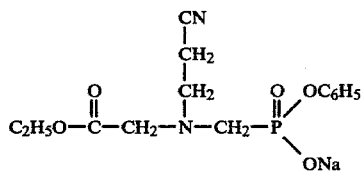

and the disodium salt of methyl N-carboxymethyl-N-phosphonomethyl-β-alaninate which has the formula

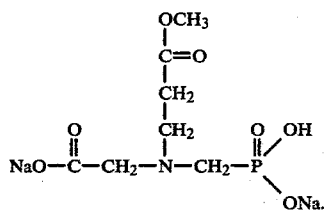

The preparation of each of these compounds is described in the examples which follow.

EXAMPLE 1

A suitable reaction vessel was charged with 2.7 grams (0.01 mole) of ethyl N-(hydroxy)phenoxyphosphonomethylglycinate in 10 ml. of water. The solution was cooled and treated with 0.8 grams of 50% aqueous sodium hydroxide, after which 5.0 grams (0.095 mole) of acrylonitrile was added. After 3 days, the excess acrylonitrile layer was removed and discarded. The aqueous layer was rotoevaporated to dryness, redissolved in a little water and treated with excess ethanol. A minor amount of precipitate which formed overnight was filtered off, and further ethanol was added to the filtrate. After 3 days the mixture was concentrated to dryness and dried in a dessicator over potassium hydroxide pellets. The product, obtained as a brittle light amber glass, was 2.8 grams of the monosodium salt of ethyl N-(2-cyanoethyl)-N-phenoxyphosphonomethylglycinate. Elemental analysis showed 8.34% nitrogen and 9.43% phosphorus as against calculated values of 8.04% and 8.89% for $C_{14}H_{18}N_2NaO_5P$.

EXAMPLE 2

A suitable reaction vessel was charged with 16.9 grams (0.10 mole) of N-phosphonomethylglycine in 30 ml. of water and 16.0 grams (0.20 mole) of 50% aqueous sodium hydroxide with stirring and cooling at about 20° C. to give a solution of the disodium salt of N-phosphonomethylglycine. With the pH maintained at about 7, a 10.0 gram (0.1 mole) portion of methyl acrylate was added to the salt solution, and the mixture was rotated on a wheel for about 4 days at 20°-25° C. The methyl acrylate layer was removed and discarded, and the aqueous layer was extracted with ether. The aqueous solution was then concentrated to dryness at 10°-20° C./1-2 mm., and the glass obtained was broken up and redried over potassium hydroxide pellets in a dessicator at <1 mm. The product obtained is 12.8 grams of the disodium salt of N-carboxymethyl-N-phosphonomethyl-β-alaninate, methyl ester as a glass. Elemental analysis showed 26.69% carbon, 3.94% hydrogen, 3.97% nitrogen and 10.58% phosphorus as against calculated values of 28.11%, 4.04%, 4.68% and 10.35% for $C_7H_{12}NNa_2O_7P$.

The post-emergent herbicidal activity of each of the compounds of this invention is demonstrated as follows. The active ingredient is applied in spray form to 14-21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergent herbicidal activity index used in Tables I and II is as follows:

| Plant Respones | Index |
| --- | --- |
| 0-24% Inhibition | 0 |
| 25-49% Inhibition | 1 |
| 50-74% Inhibition | 2 |
| 75-99% Inhibition | 3 |
| All Killed | 4 |
| Species not present | * |

In said Tables, the compounds are designated by the Example numbers, WAT indicates weeks after treatment, and the plant species treated are each represented by a code letter as follows:

| | |
| --- | --- |
| A - Canada Thistle | K - Barnyardgrass |
| B - Cocklebur | L - Soybean |

-continued

| | |
|---|---|
| C - Velvetleaf | M - Sugar Beet |
| D - Morningglory | N - Wheat |
| E - Lambsquarters | O - Rice |
| F - Smartweed | P - Sorghum |
| G - Yellow Nutsedge | Q - Wild Buckwheat |
| H - Quackgrass | R - Hemp Sesbania |
| I - Johnsongrass | S - Panicum Spp |
| J - Downy Brome | T - Crabgrass |

The unexpected level of herbicidal activity of the compounds herein is demonstrated by the inclusion in Table I of the data obtained in the above-described test with the related compound listed below. Such related compounds are designated in the Table by the R numbers shown.

R 1: the monosodium salt of N-(2-cyanoethyl)-N-phosphonomethylglycine

R 2: N-(2-carboxyethyl)-N-phosphonomethylglycine

R 3: the disodium salt of N-(2-carbamoylethyl)-N-phosphonomethylglycine

R 4: the monosodium salt of ethyl N-(2-cyanoethyl)-N-ethoxyphosphonomethylglycinate

TABLE I

| Compound | WAT | kg h | A | B | C | D | E | F | G | H | I | J | K |
|---|---|---|---|---|---|---|---|---|---|---|---|---|---|
| 1 | 2 | 11.2 | 3 | 2 | 1 | 0 | 2 | 3 | 1 | 1 | 1 | 2 | 3 |
|  | 4 | 11.2 | 2 | 3 | 2 | 1 | 3 | 3 | 2 | 2 | 4 | 4 | 4 |
|  | 2 | 5.6 | 2 | 2 | 2 | 1 | 2 | 4 | 1 | 1 | 3 | 1 | 3 |
|  | 4 | 5.6 | 3 | 4 | 4 | 2 | 3 | 4 | 3 | 2 | 3 | 2 | 4 |
| 2 | 2 | 11.2 | 1 | 2 | 2 | 1 | 4 | 4 | 1 | 2 | 1 | 3 | 3 |
|  | 4 | 11.2 | 2 | 3 | 3 | 2 | 4 | 4 | 2 | 3 | 2 | 3 | 4 |
|  | 2 | 5.6 | 1 | 2 | 2 | 1 | 3 | 3 | 1 | 1 | 1 | 2 | 2 |
|  | 4 | 5.6 | 2 | 2 | 2 | 1 | 3 | 3 | 1 | 1 | 1 | 2 | 3 |
| R 1 | 2 | 11.2 | 1 | 1 | 1 | 1 | 2 | 2 | 1 | 1 | 0 | 0 | 2 |
|  | 4 | 11.2 | 1 | 2 | 1 | 1 | 4 | 1 | 2 | 1 | 3 | 1 | 2 |
|  | 2 | 5.6 | 1 | * | 1 | 1 | 1 | 1 | 1 | 1 | 0 | 0 | 0 |
|  | 4 | 5.6 | 1 | * | 1 | 1 | 1 | 2 | 1 | 0 | 2 | 1 | 1 |
| R 2 | 2 | 11.2 | 0 | 2 | 1 | 2 | 1 | 0 | 1 | 0 | 0 | 0 | 1 |
|  | 4 | 11.2 | 0 | 2 | 0 | 2 | 1 | 0 | 0 | 0 | 1 | 0 | 0 |
| R 3 | 2 | 11.2 | 1 | 1 | 1 | 1 | 2 | 2 | 2 | 1 | 1 | 1 | 2 |
|  | 4 | 11.2 | 2 | 1 | 0 | 2 | 2 | 2 | 2 | 1 | 0 | 0 | 2 |
| R 4 | 2 | 11.2 | 0 | 0 | 0 | 0 | 0 | 0 | 0 | 0 | 0 | 0 | 0 |
|  | 2 | 5.6 | 0 | 0 | 0 | 0 | 0 | 0 | 0 | 0 | 0 | 0 | 0 |

TABLE II

| Compound | WAT | kg h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 3 | 3 | 3 | 2 | 2 | 3 | 4 | 2 | 1 | 3 | 4 | 3 | 2 | 3 | 3 | 3 |
|  | 4 | 5.6 | 3 | 4 | 4 | 3 | 3 | 3 | 4 | 3 | 2 | 4 | 4 | 4 | 4 | 3 | 3 |
|  | 2 | 1.12 | 1 | 3 | 0 | 0 | 1 | 1 | 0 | 1 | 1 | 1 | 1 | 1 | 0 | 1 | 1 | 2 |
|  | 4 | 1.12 | 1 | 3 | 2 | 1 | 3 | 2 | 1 | 1 | 1 | 2 | 2 | 2 | 0 | 2 | 2 | 3 |
|  | 2 | 0.28 | 1 | 1 | 1 | 0 | 1 | 1 | 0 | 1 | 0 | 3 | 2 | 1 | 0 | 2 | 1 | 2 |
|  | 4 | 0.28 | 1 | 3 | 2 | 0 | 2 | 1 | 0 | 1 | 0 | 3 | 3 | 1 | 0 | 3 | 3 | 3 |
|  | 2 | 0.06 | 1 | 1 | 0 | 0 | 1 | 0 | 0 | 0 | 0 | 0 | 0 | 1 | 0 | 0 | 0 |
| 2 | 2 | 5.6 | 1 | 1 | 1 | 1 | 2 | 2 | 1 | 1 | 0 | 3 | 1 | 2 | 2 | 3 | 2 | 3 |
|  | 4 | 5.6 | 2 | 2 | 1 | 2 | 2 | 2 | 2 | 2 | 1 | 4 | 2 | 3 | 3 | 3 | 2 | 3 |
|  | 2 | 1.12 | 1 | 1 | 1 | 1 | 1 | 1 | 1 | 1 | 0 | 1 | 1 | 1 | 0 | 1 | 1 | 2 |
|  | 4 | 1.12 | 1 | 1 | 1 | 1 | 1 | 1 | 1 | 1 | 0 | 1 | 1 | 1 | 1 | 1 | 1 | 2 |
|  | 2 | 0.28 | 1 | 0 | 1 | 0 | 0 | 0 | 0 | 0 | 0 | 1 | 0 | 0 | 0 | 0 | 0 | 0 |

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amines, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acyl)taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Although compositions of this invention can also contain other additaments, for example, fertilizers, phytotoxicant and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the active ingredient are applied to above-ground portions of plants. The application of liquid and particulate solid herbicidal compositions to above-ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where inhibition of the aquatic plants is desired.

The application of an effective amount of the compounds of this invention to the plant is essential and critical for the practice of the present invention. The exact amount of active ingredient to be employed is dependent upon such factors as the plant species and stage of development thereof, and the amount of rainfall as well as the specific compound employed. In foliar treatment for the inhibition of vegetative growth, the active ingredients are applied in amounts from about 0.28 to about 22.4 or more kilograms per hectare. In applications for the inhibition of aquatic plants, the active ingredients are applied in amounts of from about 0.1 parts per million to about 1000 parts per million, based on the aquatic medium. An effective amount for phytotoxic or herbicidal action is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound selected from (a) the monosodium salt of ethyl N-(2-cyanoethyl)-N-phenoxyphosphonomethylglycinate and (b) the disodium salt of methyl N-carboxymethyl-N-phosphonomethyl-$\beta$-alaninate.

2. A compound as defined in claim 1 which is the monosodium salt of ethyl N-(2-cyanoethyl)-N-phenoxyphosphonomethylglycinate.

3. A compound as defined in claim 1 which is the disodium salt of methyl N-carboxymethyl-N-phosphonomethyl-$\beta$-alaninate.

4. A herbicidal composition comprising an inert adjuvant and a herbicidally effective amount of a compound of claim 1.

5. A herbicidal composition comprising an inert adjuvant and a herbicidally effective amount of a compound of claim 2.

6. A herbicidal composition comprising an inert adjuvant and a herbicidally effective amount of a compound of claim 3.

7. A herbicidal method which comprises applying to plants a herbicidally effective amount of a compound of claim 1.

8. A herbicidal method which comprises applying to plants a herbicidally effective amount of a compound of claim 2.

9. A herbicidal method which comprises applying to plants a herbicidally effective amount of a compound of claim 3.

* * * * *